United States Patent [19]

Schulz

[11] Patent Number: 5,167,965
[45] Date of Patent: Dec. 1, 1992

[54] PALATABLE CHOLESTYRAMINE GRANULES, TABLETS AND METHODS FOR PREPARATION THEREOF

[75] Inventor: Gary J. Schulz, Midland, Mich.

[73] Assignee: The Dow Chemical Company, Midland, Mich.

[21] Appl. No.: 521,797

[22] Filed: May 10, 1990

Related U.S. Application Data

[63] Continuation-in-part of Ser. No. 140,696, Jan. 4, 1988, abandoned, which is a continuation-in-part of Ser. No. 12,470, Feb. 9, 1987, abandoned.

[51] Int. Cl.$^5$ .................. A61K 9/14; A61K 47/36
[52] U.S. Cl. .................. 424/499; 424/500; 424/494
[58] Field of Search ............ 424/79, 483, 485, 494, 424/500, 499

[56] References Cited

U.S. PATENT DOCUMENTS

| | | | |
|---|---|---|---|
| 3,308,020 | 3/1967 | Wolf et al. ............ | 167/65 |
| 3,383,281 | 5/1968 | Wolf et al. ............ | 167/65 |
| 3,499,960 | 3/1970 | Macek et al. ........... | 424/33 |
| 3,627,872 | 4/1968 | Parkinson .............. | 424/79 |
| 3,769,399 | 10/1973 | Hagerman et al. ....... | 424/79 |
| 3,780,171 | 12/1973 | Irmscher et al. ........ | 424/79 |
| 3,787,474 | 1/1974 | Daniels et al. ......... | 260/459 |
| 3,846,541 | 11/1974 | Howard ................. | 424/79 |
| 3,962,420 | 6/1976 | Seidel et al. .......... | 424/81 |
| 3,974,272 | 8/1976 | Polli et al. ........... | 424/78 |
| 3,980,770 | 9/1976 | Ingelman et al. ........ | 424/79 |
| 4,140,652 | 2/1979 | Korshak et al. ......... | 252/426 |
| 4,172,120 | 10/1979 | Todd et al. ............ | 424/44 |
| 4,198,395 | 4/1980 | DeSimone ............... | 424/79 |
| 4,198,396 | 4/1980 | Seidel et al. .......... | 424/81 |
| 4,230,687 | 10/1980 | Sair et al. ............ | 424/22 |
| 4,478,819 | 10/1984 | Hercelin et al. ........ | 424/37 |
| 4,600,645 | 7/1986 | Ghebre-Sellassie et al. | 428/403 |
| 4,687,662 | 8/1987 | Schobel ................ | 424/44 |
| 4,695,463 | 9/1987 | Yang et al. ............ | 424/440 |
| 4,747,881 | 5/1988 | Shaw et al. ............ | 106/209 |

FOREIGN PATENT DOCUMENTS

| | | |
|---|---|---|
| 0190826 | 1/1986 | European Pat. Off. . |
| 0227603 | 12/1986 | European Pat. Off. . |
| 1262556 | 9/1969 | United Kingdom . |
| 1446352 | 8/1973 | United Kingdom . |
| 1566609 | 3/1977 | United Kingdom . |
| 1573487 | 5/1978 | United Kingdom . |

OTHER PUBLICATIONS

Wallace Cloud, "Fast-Rising Markets for Cholesterol-Lowering Drugs", Chemical Focus 3, Nov. 1984.
"Pulverizing Machinery", Publication of Mikropul Corporation, 10 Chatham Road, Summit, N.J. 07901.
"Equipment for the Chemical Process Industries-Heat Exchanger Liquid-Solid Separation Mixing and De-lumping Size Reduction-Extructor for continuous mixing of solids with Liquids or Gases", Rietz Division, Bepex Corporation, P.O. Box 880, Santa Rose, Calif. 95402.

Primary Examiner—Paul R. Michl
Assistant Examiner—LaVonda R. DeWitt

[57] ABSTRACT

Palatable cholestyramine granules, tablets and method for preparation thereof are disclosed.

14 Claims, 4 Drawing Sheets

PALATABLE CHOLESTYRAMINE GRANULES, TABLETS AND METHODS FOR PREPARATION THEREOF

CROSS-REFERENCE TO RELATED APPLICATIONS

This is a continuation-in-part of abandoned U.S. application Ser. No. 07/140,696, filed Jan. 4, 1988, which is a continuation-in-part of U.S. application Ser. No. 012,470, filed Feb. 9, 1987, which has been abandoned.

BACKGROUND OF THE INVENTION

Cholestyramine is a compound known to be effective in controlling hypocholesteremia, also known as high blood cholesterol levels, believed to be responsible in many cases for arteriosclerosis as described in U.S. Pat. No. 3,383,281. Cholestyramine, which is orally consumed in order to effect its cholesterol lowering or controlling properties, is astringent and unpleasant to swallow. The cholestyramine also has the side effect of inducing constipation.

Processes and compositions are known such as those described in U.S. Pat. Nos. 3,308,020; 3,499,960; and 3,947,272. For example, U.S. Pat. No. 3,974,272 teaches combining cholestyramine with a modified gum, together with a flavoring agent to form a coascervate in an aqueous medium such as water, milk, and fruit juice. Although pharmaceutically effective, these known compositions are still very undesirable to drink, since the compositions form a gritty coating on the surface inside of the mouth and require at least an additional glass of water to rinse off the gritty coating. Another disadvantage is that the solids of such compositions, including the cholestyramine particles, quickly settle after being added to the aqueous medium, requiring the consumer to frequently stir the medium in order to maintain the cholestyramine in suspension. Another disadvantage of the compositions prepared in accordance with U.S. Pat. No. 3,947,272 is that they do not readily disperse when added to an aqueous medium. Instead, clumps form which require several minutes stirring before the drink can be consumed. Such disadvantages become particularly pronounced for individuals who need to consume the cholestyramine compositions several times a day for periods of months or even years.

Evidence of the unpalatability of cholestyramine compositions currently being marketed is the low rate of compliance by patients to adhere to a diet requiring daily consumption of the cholestyramine product. This low compliance rate indicates a definite need for a cholestyramine composition which is more palatable than the known compositions.

SUMMARY OF THE INVENTION

In one embodiment of the present invention is disclosed a process for preparing a palatable cholestyramine composition, comprising (a) forming a paste of cholestyramine, a gum and water;
(b) extruding the paste to form an extrudate;
(c) drying the extrudate; and
(d) pulverizing the dried extrudate to form dry, water-dispersible granules, wherein said granules comprise cholestyramine particles immobilized by the gum wherein both the cholestyramine particles and the gum are discontinuous phases throughout the granules such that the cholestyramine particles are not encased by the gum such that when the granules are added to an aqueous media approximately the same number of cholestyramine particles remain immobilized by the gum.

In another embodiment of the present invention are disclosed granules or tablets comprising cholestyramine particles immobilized by a gum wherein both the cholestyramine particles and the gum are discontinuous phases throughout the granules or tablets such that the cholestyramine particles are not encased by the gum such that when the granules or tablets are added to an aqueous media approximately the same number of cholestyramine particles remain immobilized by the gum.

In yet another embodiment of the present invention is disclosed a method for treating a mammal suffering from hypocholesteremia comprising orally administering to said patient a composition comprising (a) an aqueous medium which is water, milk, fruit juice, or soft drinks; and
(b) granules comprising a pharmaceutically effective amount of cholestyramine particles immobilized by a gum wherein both the cholestyramine particles and the gum are discontinuous phases throughout the granules such that the cholestyramine particles are not encased by the gum such that when the granules are added to the aqueous media approximately the same number of cholestyramine particles remain immobilized by the gum.

The present invention has the advantage of providing granules or tablets which are more palatable than known compositions containing cholestyramine. Another advantage of the present invention is that the granules prepared therefrom are larger than granules taught in known compositions and allow for improved palatability. Another advantage of the present invention is that it provides granules which are much more readily dispersible in an aqueous medium, do not clump, and require only a few seconds stirring before the drink is consumed. And still yet another advantage of the present invention is that it provides granules and tablets, which when added to an aqueous medium, remain suspended in the medium and require little or no stirring thereafter.

DETAILED DESCRIPTION OF THE EMBODIMENTS

Figure 1:
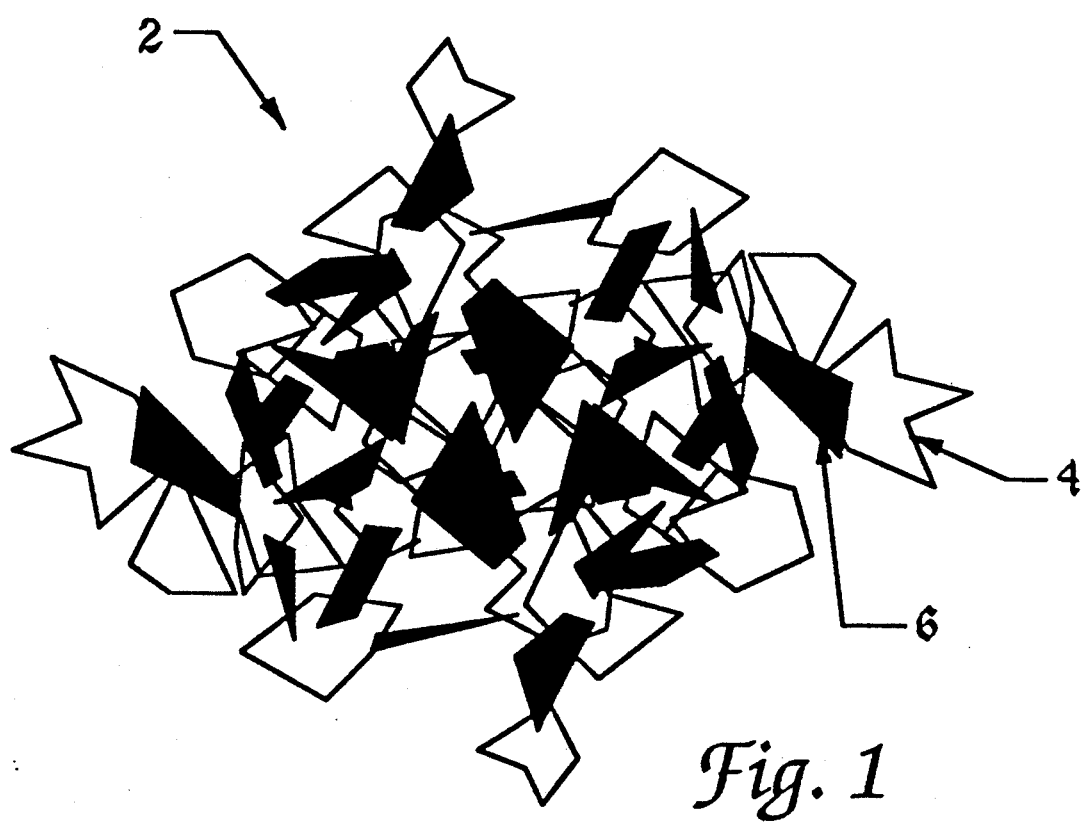

In FIG. 1 is shown an enlargement of a microscopic sketch of the wet heterogeneous paste 2 used to prepare granules or tablets of the cholestyramine composition of the present invention. Paste 2 is made of swollen cholestyramine particles 4 and swollen gelled gum 6, each of which is present discontinuously throughout paste 2. The swelling of the cholestyramine particles 4 is due to the absorption of water. The swelling of gum 6 occurs upon the expelling of water from the swollen cholestyramine 4.

Figure 2:
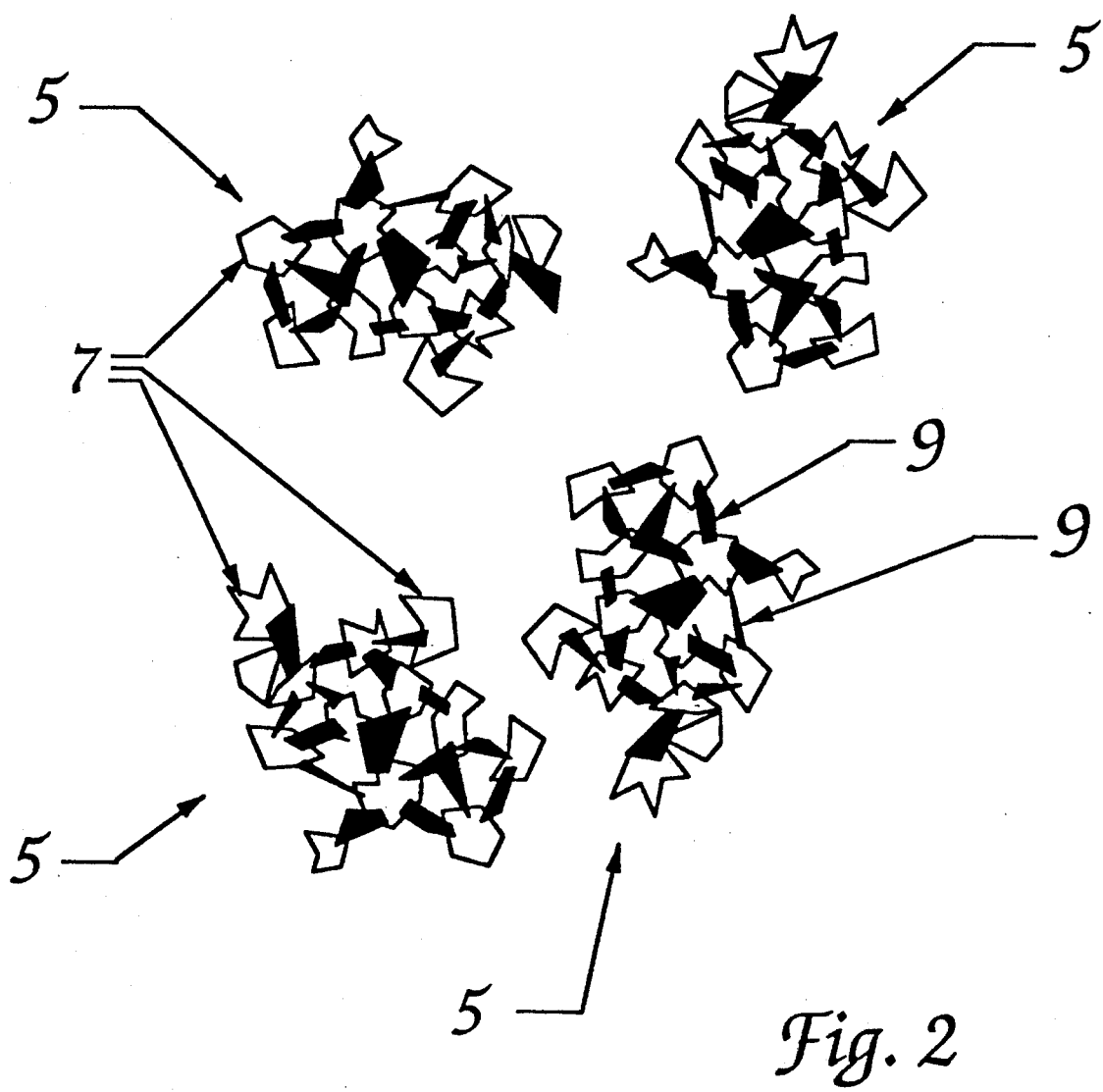

In FIG. 2 is shown an enlargement of a microscopic sketch of dry, water-dispersible granules 5. Granules 5 are formed by removal of most of the water from paste 2 in FIG. 1, followed by subsequent pulverization to smaller-sized granules 5 ($\leq 3000$ microns ($\mu$), i.e., 3 mm or less). After removal of the water, cholestyramine particles 7 in dry granule 5 remain immobilized by gum 9 wherein both the cholestyramine particles 7 and the gum 9 are discontinuous phases such that the cholestyramine particles 7 are not encased by the gum 9.

Figure 3:
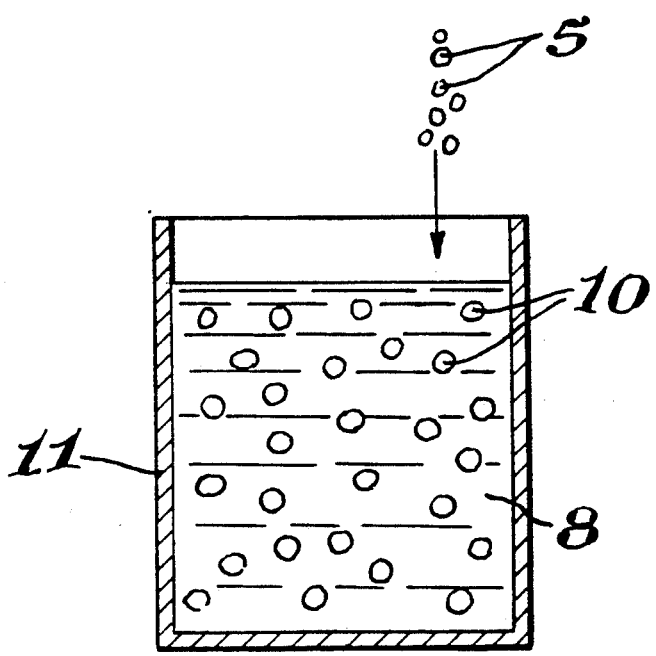

In FIG. 3 is shown a container 11, such as a drinking glass, containing an aqueous medium 8 wherein dry granules 5 are added to and dispersed in the aqueous medium to form water swollen granules 10. Water swollen granules 10 maintain their identity with the dry granule 5 from which each is derived, since the gum in each swollen granule 10 still immobilizes approximately the same number of cholestyramine particles.

Figure 4:
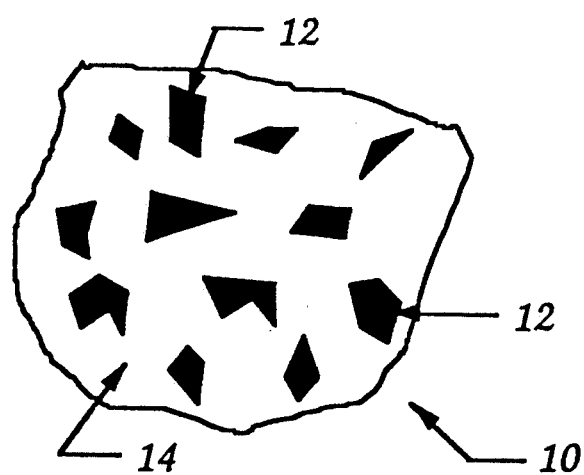

In FIG. 4, individual water swollen granule 10 comprises swollen cholestyramine particles 12 which remain immobilized by a swollen gum 14 which is present continuously throughout water swollen granule 10. Approximately the same number of cholestyramine particles are occluded within water swollen granule 10 as from dry granule 5 from which water swollen granule 10 is derived. Granule 10 is about 75–3000 $\mu$ in diameter, more preferably from about 300–1000 $\mu$.

The term "cholestyramine" or "cholestyramine particle" is intended to mean a synthetic, strongly basic anion exchange resin containing quaternary ammonium functional groups which are attached to a styrene-divinylbenzene copolymer, such as described in U.S. Pat. Nos. 3,308,020: 3,383,281; 3,499,960: and 3,974,272 cited hereinbefore. Cholestyramine is known to be effective in controlling the level of blood cholesterol.

Although cholestyramine is the most preferred cholesterol controlling or lowering agent, the process of the present invention can be used to prepare palatable granules or tablets of any solid cholesterol controlling or reducing compound which is relatively water insoluble, is gritty, and/or has charged surfaces.

The term "flavoring agent" is intended to mean a reagent which imparts a flavor to the compositions of the present invention to improve their palatability.

The term "gum" is meant to mean hydrophobic colloid of carbohydrates such as methylcellulose, ethylcellulose, sodium carboxymethyl cellulose, hydroxyethyl cellulose, hydroxypropyl cellulose and charged anionic gums such as carrageenan, sodium alginate, potassium alginate, propylene glycol alginate, Xantham, gum arabic, agar and pectins. Of particular preference is hydroxypropyl methylcellulose and methylcellulose, most preferably methylcellulose. Synthetic gums include polyvinyl alcohol and polyvinyl pyrrolidone starch. Viscous gums are preferred over less-viscous gums due to the higher bonding efficiency of the viscous gums to the cholestyramine particles to form more stable water-dispersible granules or tablets. Generally, viscous gums tend to have a higher molecular weight than less viscous gums. Generally, the viscosity of the gum can range between about 5 to about 400,000 centipoise, preferably from about 4000 to about 100,000, based upon a 2 percent by weight solution of the gum in water. Viscosities of the gum can be determined by known methods, such as those described in *U.S. Pharmacopeia National Formulary*, Volume XXI, USP, Procedure 911, page 1278.

The term "immobilized" refers to the bonding of the cholestyramine particle by the gum, either dry or swollen, such that the relative movement of approximately the same number of cholestyramine particles associated with the gum is hindered, especially from leaving either the dry or swollen granule.

The term "aqueous medium" is meant to mean any medium containing water within which cholestyramine granules can be dispersed. Representative aqueous mediums which can be employed in the practice of this invention are water, milk, and fruit juices such as orange, grapefruit, tomato, pineapple and the like, and soft drinks such as colas, sodas, pops, uncolas and the like.

The term "swollen" is meant to mean the expansion of size or volume of cholestyramine or gum particles beyond their dry size or volume.

The term "gel" is meant to mean hydrating a substance to the extent that it does not tend to flow under its own weight, but does flow upon external mechanical force.

The term "dry granule" is meant to mean granules approximately devoid of water in which cholestyramine is immobilized by a gum. When the dry granules are added to an aqueous media, approximately the same number of cholestyramine particles continue to remain immobilized by the gum even though the entire granule is swollen with water. Generally, the dry granules have a particle size diameter ranging from about 3000 to about 50 $\mu$, preferably from about 850 to about 100 $\mu$, more preferably from about 250 to about 100 $\mu$.

The term "water swollen granule" is meant to mean particles of swollen cholestyramine immobilized by a swollen gum phase.

The term "paste" as used herein is meant to mean the mixture of cholestyramine and the gum which has been moistened with sufficient water to form a soft, viscous mass of cholestyramine particles and gelled gum, each of which is present discontinuously throughout the paste, i.e., the cholestyramine is dispersed as a discontinuous phase and is held together by particles of the gum which are also dispersed as a discontinuous phase. The cholestryamine particles are not surrounded or encased by the gum, but the cholestryamine particles are sufficiently held together to prevent mobility of the particles. The mixture of cholestyramine and gum is moistened with sufficient water to form a paste containing from about 50 to about 95 percent water (weight basis), preferably from about 65 to about 75 percent by weight water, most preferably about 70 percent.

The term "encase" as used herein is meant to mean the complete enclosure or total surrounding of the cholestryamine particles by the gum.

The number of cholestyramine particles immobilized per dry granule can vary greatly, depending in part upon the size of the cholestyramine particles and the size or diameter of the granule. Generally, the smaller the cholestyramine particle the larger the number of cholestyramine particles that can be immobilize by gum in the granule. Similarly, larger granules can accommodate a greater number of cholestyramine particles. The following Table gives an estimation of the number of cholestyramine particles for various sized granules assuming a fixed cholestyramine particle size diameter of 50 $\mu$.

| Granule Mesh Size | Granule Diameter Size ($\mu$) | Number of Cholestyramine Particles |
|---|---|---|
| 20 | 850 | 2457 |
| 35 | 500 | 500 |
| 60 | 250 | 62 |
| 80 | 180 | 23 |
| 100 | 150 | 13 |

One feature of granules of the present invention is that upon their application to an aqueous medium they do not coacervate or form coacervate solutions within minutes as taught in U.S. Pat. No. 3,974,272. That is, in U.S. Pat. No. 3,974,272 the cholestyramine particles are free to flow to form loosely held small clumps from suspension. In comparison, the cholestyramine particles in Applicant's granules are generally not free to flow and do not form small clumps since they are already immobilized by the gum. Also, U.S. Pat. No. 3,974,272 teaches the gum is the flocculant which loosely adheres or flocs the cholestyramine particles. Contrariwise, in Applicant's claimed invention, the gum is generally not available for flocculating the cholestyramine particles since the gum is already immobilizing the cholestyramine particles in the granule.

Granules or tablets of the present invention, optionally and preferably, contain a small amount of a flavoring, such as strawberry, orange, grape, raspberry, lemon, lime, cherry, licorice, spearmint, wintergreen, chocolate, eggnog, butterscotch, vanilla, banana, and the like, in order to enhance the sweetness or flavor of aqueous compositions prepared therefrom. Flavoring agents such as sucrose or fructose sugars or such as aspartame can be employed to improve sweetness. Such natural and artificial flavorings are well known and all are suitably employed herein. Citric acid is commonly employed in conjunction with fruit flavorings. The flavoring agent can comprise from about 1 to about 90 weight percent of the composition, preferably about 70 to 80 percent. The flavoring agent can be blended with the dry granules in order to prepare the compositions of the present invention. Alternatively, the flavoring reagent can be mixed with the wet paste prior to preparation of the granules. Liquid or oily flavors may be employed herein so long as they are thoroughly mixed with the other components of the cholestyramine mixture in a way that the cholestyramine mixture is a dispersible particulate. Such oily flavorings often improve the dispersibility of the gum due to their hydrophobic character.

The manner in which the paste is prepared is not critical to the invention. Preferably, dry cholestyramine is admixed with dry gum to form a mixture or blend which can be moistened to the requisite water content, forming the paste. Alternatively, the gum can be moistened to the requisite water content before addition of the cholestyramine. Conversely, the cholestyramine can be moistened first to the requisite water content before addition of the gum. Alternatively, cholestyramine, gum, and water can be admixed simultaneously in order to prepare the paste.

Cholestyramine is admixed with the gum in a ratio ranging from about 10 to about 0.1 parts by weight of cholestyramine to one part of gum, preferably from about 1 to 4 parts by weight of cholestyramine to one part by weight gum, most preferably 2 parts by weight cholestyramine to one part gum.

The paste used in preparing the compositions of the present invention are conveniently and preferably prepared in a device known as an Extructor®, trademark of the Rietz Division, Bepex Corporation, Santa Rosa, CA. The Extructor® is adaptable to the continuous mixing of solids and liquids where very viscous pastes and plastic masses are handled.

After the paste is prepared, it is wet extruded into strands which are then chopped into wet pellets. The water content of the paste should not be so high that the extrudate strands formed therefrom (as by an extruder) readily stick together and reagglomerate or that they become fragile or "runny". Such pellets can range from about 0.001 to about 0.5 centimeters (cm) in diameter.

The wet pellets are conveniently dried by any convenient method, such as by air drying or oven drying.

The dry pellets can be pulverized into the desired water dispersible granules by any suitable method or device of such purpose. For example, the dry pellets can be pulverized into water-dispersible granules of the desired particle size with a device such as the Micro ACM pulverizer of the Mikropul Corporation, Summit, New Jersey.

Alternatively, the paste, wet pellets or dry granules, as prepared hereinabove, can be pressed directly into a tablet using any known method or device.

The tablets of the present invention can be made even more palatable by the further addition of base such as sodium bicarbonate together with a suitable organic acid such as citric acid or ascorbic acid. The addition of moisture either by water or saliva will cause the bicarbonate to contact the citric or ascorbic acid and form gaseous carbon dioxide. The formation of the carbon dioxide aids in the disintegration of the tablet in the mouth, improving chewability or palatability. When added to aqueous media, the formation of the carbon dioxide aids the dispersion of the tablet in water. Approximately equivalent ratios of base to acid are employed. For example, one mole of citric acid has three equivalents of acid, and would require three moles of sodium bicarbonate (which has one equivalent base per mole) to neutralize both the acid and base. The combined amounts of acid and base present in the tablet can range from about 1 to about 20 percent by weight, preferably between about 1 to about 5 percent by weight.

Once prepared, the dry granules or tablets can be added to about 6 to about 8 ounces of an aqueous medium to make a non-gritty tasting slurry that sticks to the sides of the mouth much less than compositions previously taught. After an extended period of time, the swollen gum likely will continue to swell with water, thereby lowering the viscosity of the gum to the point the highly swollen gum may no longer be capable of immobilizing the swollen cholestyramine particles. Under a normal period for consumption (i.e. within several minutes), it is anticipated the compositions containing the cholestyramine particles will be consumed long before the gum is too swollen to immobilize the cholestyramine particles. The slurry thus prepared can be consumed within zero to about 60 minutes after the granules have been added to the aqueous medium, preferably from about zero to 10 minutes.

Where the granules or tablets are to be orally administered in an aqueous medium, the recommended dose of cholestyramine is about 4 to about 12 grams (g) three times a day. The recommended dosage of the gum is from about one to about 2 g three times a day, especially for methylcellulose as a bulking laxative.

The following examples illustrate the present invention and the manner by which it can be practiced but, as such, should not be construed as limitations upon the overall scope of the same.

EXAMPLE 1

PREPARATION OF GRANULATED CHOLESTYRAMINE/-METHYLCELLULOSE ETHER POWDERED BLEND

Approximately 10 lbs of a heterogeneous mixture is made by first blending three parts cholestyramine powder with one part Methocel ® A4M, trademark of The Dow Chemical Company, Midland, MI. Methocel ®

A4M is an untreated powder o methylcellulose ether having a viscosity of 4000 centipoise. To this powder blend water is added to make a paste having a water content of about 75 percent. The water proportionates between the cholestyramine and the Methocel® powder. The cholestyramine swells, but does not dissolve. The Methocel® powder hydrates and dissolves forming a gelled gum which is present discontinuously throughout the paste to immobilize the cholestyramine particles.

This heterogeneous paste is then extruded with an RE-6 Extructor® with 1/16 inch die holes, and the moist extrudate is chopped into wet pellets. The wet pellets are dried in a tray dryer and ground with a 6 inch Wiley knife mill using a 20 mesh (U.S. Standard) internal screen to the following particle size distribution:

| Mesh | Percent On Screen |
| --- | --- |
| 16 | 0.0 |
| 20 | 1.3 |
| 30 | 32.7 |
| 40 | 29.2 |
| 60 | 21.3 |
| 80 | 3.7 |
| 100 | 1.6 |
| 140 | 1.9 |
| PAN | 5.0 |

A cut from 30 to 60 mesh is obtained by screening. Generally, a 35 mesh is equivalent to about 500 microns and a 60 mesh is equivalent to about 250 microns. The cut is blended with a flavoring agent base at about 2.7 parts of the cut to 8.0 parts flavoring agent base. Then about 21 g of this blend is mixed in approximately 6 ounces (oz) water to form a smooth, good tasting orange drink with good palatability.

EXAMPLE 2

SIMULTANEOUS WETTING/EXTRUSION OF POWDERED BLEND OF CHOLESTYRAMINE/METHYLCELLULOSE

One part Methocel® A4M powder having a viscosity of 4000 centipoise is blended with two parts cholestyramine powder at a weight ratio of 1:2, respectively. As this blend is fed to an RE-6 Extructor® at a rate of 56.2 pounds per hour (lbs/hr), water is fed to the Extructor® at 131 lbs/hr to form a heterogeneous paste mixture having a moisture content of 70 percent. This paste is extruded into moist 1/16 inch diameter strands which are chopped into ⅛ inch to ¾ inch pellets. The pellets are dried in a fluid bed dryer and ground with a Mikropulverizer 10 ACM granules mill to the following particle size distribution:

| Mesh Size | Granule Diameter (μ) | Accumulative Percent |
| --- | --- | --- |
| 30 | 600 | 18.5 |
| 40 | 425 | 38.7 |
| 45 | 355 | 55.3 |
| 60 | 250 | 70.3 |
| 80 | 180 | 79.3 |
| 100 | 150 | 83.7 |
| 140 | 106 | 87.8 |
| 200 | 75 | 91.3 |

The 35-80 mesh fraction is blended with an orange flavoring agent (6 parts 35-80 mesh fraction/16 parts flavoring agent). About 22 g of the flavored granules are mixed with 4 to 10 oz. water to form a palatable, good tasting orange drink.

EXAMPLE 3

A 7.25 g portion of the cholestyramine/methylcellulose granules from the 35-80 mesh fraction containing a flavoring agent prepared as in Example 2 is compressed into a ¼ inch by 1 ¼ inch diameter tablet at a pressure of 4000 pounds per square inch (psi). Four of these tablets are equivalent to a pharmaceutically acceptable dosage for an adult. The tablets can be chewed without water.

EXAMPLE 4

Four tablets of cholestyramine/methylcellulose prepared as in Example 3 are added to 4 to 10 oz. of water and briefly stirred. Within 1 to 2 minutes the tablets disperse, forming a smooth, good tasting orange drink.

EXAMPLE 5

A 252 g portion of Methocel® K100M having a viscosity of 100,000 centipoise is hydrated with 434 g of cold water. Then 3.86 kilograms (kg) of wet (73.8 percent by weight water) cholestyramine is mixed into the prehydrated Methocel® K100M. This mixture is then extruded with an RE-6 Extructor though 1/16 inch die holes. The extruded strands are chopped up into ⅛ inch to ¾ inch pellets. The pellets are dried in a tray dryer and milled with an Alpine 100 UPZ mill. The milled material is screened to give a 35 to 80 mesh product. Flavors are added to these granules to give a palatable good tasting drink.

What is claimed is:

1. A process for preparing a palatable cholestyramine composition comprising:
   (a) forming a paste of cholestyramine, a gum, and water, wherein dry cholestyramine is admixed with dry gum to form a mixture before moistening with water;
   (b) extruding the paste to form an extrudate;
   (c) drying the extrudate; and
   (d) pulverizing the dried extrudate to form dry, water-dispersible granules, wherein said granules comprise cholestyramine particles immobilized by the gum wherein both the cholestyramine particles and the gum are discontinuous phases throughout the granules such that the cholestyramine particles are not encased by the gum such that when the granules are added to an aqueous media, approximately the same number of cholestyramine particles remain immobilized by the gum.

2. The process of claim 1 wherein the ratio of cholestyramine to gum in the past ranges from about 10 to about 0.1 parts by weight cholestyramine to one part by weight gum.

3. The process of claim 1 wherein the ratio of cholestyramine to gum in the paste ranges from about 1 to about 4 parts by weight cholestyramine to one part by weight gum.

4. The process of claim 1 wherein said paste contains from about 45 to about 90 percent by weight water.

5. The process of claim 1 wherein said paste contains from about 65 to about 75 percent by weight water.

6. The process of claim 1 wherein said paste contains about 70 percent by weight water.

7. The process of claim 1 wherein said extrudate is chopped into wet pellets.

8. The process of claim 7 wherein the pellets range from about 0.001 to about 0.5 centimeters in diameter.

9. The process of claim 1 wherein said dry granules have a particle size ranging from about 3000 microns to about 50 microns.

10. The process of claim 1 wherein said dry granules have a particle size ranging from about 850 microns to about 100 microns.

11. The process of claim 1 wherein said dry granules have a particle size ranging from about 250 microns to about 100 microns.

12. The process of claim 1 wherein said dry granules are pressed into tablets.

13. The process of claim 1 further comprising mixing a flavoring agent to the paste prior to extruding the paste.

14. The process of claim 13 wherein the flavoring agent is sugar, citric acid, potassium citrate, orange flavor, or aspartame.

* * * * *